United States Patent [19]

Ueda et al.

[11] Patent Number: 5,425,374

[45] Date of Patent: Jun. 20, 1995

[54] DEVICE AND METHOD FOR EXPIRATORY AIR EXAMINATION

[75] Inventors: Hideo Ueda, Osaka; Mitsuo Hiromoto, Kyoto, both of Japan

[73] Assignees: Hideo UEDA, Minoh; Kabushiki Kaisha Kyoto Daiichi Kagaku, Kyoto, both of Japan; a part interest

[21] Appl. No.: 70,984

[22] Filed: Jun. 3, 1993

[30] Foreign Application Priority Data

Jun. 3, 1992 [JP] Japan .................................. 4-170287
Jun. 30, 1992 [JP] Japan .................................. 4-197699

[51] Int. Cl.$^6$ ................................................ A61B 5/00
[52] U.S. Cl. ...................................... 128/719; 128/716; 73/23.3; 422/84
[58] Field of Search ................... 128/716, 719, 204.22, 128/204.23, 633, 664–666; 73/22.3; 422/84

[56] References Cited

U.S. PATENT DOCUMENTS

| | | | |
|---|---|---|---|
| 3,746,512 | 7/1973 | Kamai et al. | 422/84 |
| 4,140,106 | 2/1979 | Kirmaier | 128/719 |
| 4,178,919 | 12/1979 | Hall | 128/719 |
| 4,202,352 | 5/1980 | Osborn | 128/719 |
| 5,081,871 | 1/1992 | Glaser | 128/719 |
| 5,197,481 | 3/1993 | Fisher | 128/719 |
| 5,239,995 | 8/1993 | Estes et al. | 128/204.23 |

FOREIGN PATENT DOCUMENTS 0309666 7/1988 Germany .................... 128/719

OTHER PUBLICATIONS

K. M. Dubowski, *Breath Analysis as a Technique in Clinical Chemistry*, Clin. Chem. 20.966–972 (1974).
A. Manolis, *the Diagnostic Potential of Breath Analysis*, Clin. Chem. 29.5–15 (1983).
M. Phillips, *Breath Tests in Medicine*, Scientific American, Jul., 1992.

*Primary Examiner*—William E. Kamm
*Assistant Examiner*—Robert L. Nasser, Jr.
*Attorney, Agent, or Firm*—Darby & Darby

[57] ABSTRACT

A portable type clinical examination device using expiratory air of a patient as a sample and measuring with high accuracy and rapidity concentration of trace amounts of aimed gas components contained in the expiratory air. The clinical examination device feeds an expiratory air sample provided by a patient, fed through an expiratory air sucking portion and separated in a column to a detector which detects trace amounts of aimed gas components contained in the expiratory air sample by ionizing the aimed gas components through application of ultraviolet or radiation, so that output signals from the detector are processed and concentration of the aimed gas components is computed by use of a previously memorized working curve to provide a clinical examination data which is output on a recording device or the like.

11 Claims, 6 Drawing Sheets

DEVICE AND METHOD FOR EXPIRATORY AIR EXAMINATION

BACKGROUND OF THE INVENTION

Various clinical examinations carried out for the diagnosis, treatment or prevention of diseases are essential in contemporary medical science. Particularly, clinical biochemical examinations, for analyzing particular compounds, occupy an important position in the clinical medical science. Furthermore, following development of the basic medical sciences and advancement of analyzing techniques, attempts have been made to enlarge the extent of samples to be examined and items to be measured. Attempts have also been made at improving measurement accuracy and automating measuring techniques at various measuring stages. Such attempts include developing abbreviated rapid measurement systems for urgent or bedside measurement, or systematized measurements carried out in large-scale hospitals.

Samples used in clinical biochemical examinations at the present time are generally blood and urine.

Blood provides quite ample information and allows several hundred items to be measured. However, collecting blood causes subjects or patients physical pain and the loss of their important blood. Repeated collection of blood and a continuous measurement thereof imposes a heavy burden on the subjects or patients. In addition, analyzing the blood samples is dealt exclusively or centrally by a blood analysis center (firms specialized in blood analysis), occupying significant time from blood collection to analysis. This time delay leads to larger errors in measurement of certain blood contents, which are easily gasified or denatured. Hence, such unstable components are accurately measured only at large-scale hospitals equipped with special analyzing apparatuses.

Urine is broadly used in screening. It is relatively easily and amply collectable, but provides less information than blood does, which is a problem. Also, the method of collecting urine samples can be embarrassing to the patient, and does not facilitate continuous measurement. Urine samples are also hard to collect at times.

Other bloodless and noninvasive clinical analyzing techniques aside from the urine analyzing techniques have been developed. For example, some analyzing techniques sample other body fluids such as exudate from skin (lymph), sweat, saliva or the like, or percutaneously measure blood gas with a blood gas sensor. But, these techniques have not been broadly used, since less samples are obtainable, and measurable items are limited. Hence, the main stream of development of the clinical biochemical examination techniques is now directed to those which do not cause the subjects pain when collecting the blood sample, and which can measure a larger variety of items, typically available only in trace quantities in the blood samples.

In any case, conventional clinical biochemical examinations require considerable labor and specialized techniques for collecting, transporting, preserving, separating and analyzing samples such as blood and urine. These techniques create problems with examination accuracy. They are slow and labor intensive, and cause the subjects (patients) unnecessary pain. Solving these problems will not only be beneficial to the patients, but also to the health care professionals engaged in medical treatment.

It is said that doctors having considerable experience in medical treatment can judge the identity of diseases from distinct odors emitted by the patients, and can use the odors in treating their patients. For example, expiratory air exhaled by a patient with diabetes can smell like acetone or can have a particular sweet smell. The odor of exhaled gas from a patient with a liver sickness or leukemia might resemble that of ammonia or sulfide. However, this information is obtainable from a doctors experience: it may be judged differently by specific doctors and cannot be objectively shown by data. Also, the clinical biochemical examinations using subjects' exhaled air as samples have been put to little practical use, and basic studies thereof have not been advanced, the reasons for which are twofold.

First, there is a prejudice in the art that expiratory air is not usable as a sample for clinical biochemical examination. Second, because gases to be detected in expiratory air are quite low in concentration (ppb or ppm at the most), they are measurable only by combining a concentrating device to concentrate the trace gas component with a large-scaled high-sensitivity gas detecting device. Hence, measurement of the samples can be carried out only in a laboratory provided with special instruments and equipment, which necessitate the presence of skilled operators to operate them.

There have been only a few clinical reports that discuss expiratory gas measurement. Such clinical reports include: (1) Dubowski, K,M, Breath Analysis as a Technique in Clinical Chemistry, Clin Chem., 20.966–972, 1974, (2) Manolis,A., The Diagnostic Potential of Breath Analysis, Clin. Chem., 29. 5–15, 1983, and (3) Phillips, M., Breath Tests in Medicine, Scientific American July 1992. These reports disclose measurement and observation data only.

Expiratory air, or exhaled air, is intermittently breathed out by human (or animals) during their lives. It is readily collectable, without causing the subject physical or mental pain. This noninvasive collection technique is particularly well suited for infants and patients with serious illness or damaged consciousness. Also, since trace amounts of a volatile component of mixed venous blood flowing through the alveolar blood capillary is moved into expiratory air by gas exchange, it is inferred that expiratory air and blood are correlated with respect to the volatile component. Furthermore, examinations of expiratory air enables differential measurement of the volatile components which blood analysis could not disclose. Thus, expiratory air is an ideal sample for the clinical biochemical examination.

Expiratory air, when collected in vessels, requires considerable space for preservation and transportation and some gas components subject to examination are unstable, so that they are not well suited to the analysis path normally taken by blood samples: i.e., being first transported to the analysis center and then analyzed by the large-scale apparatuses. That is, it is highly desirable that the clinical biochemical examination using expiratory air as a sample is carried out "on-site". Expiratory air may be effectively used when the gas measurement occurs while the patient is being attended to by the measuring operator, or while the patient is connected to the measuring device. For example, bedside examination, prehospital examination in an ambulance, screening upon medical examination and monitoring of patient status (continuous monitoring) are all suitable applications.

The previously mentioned apparatus, comprising the combination of the concentrating device and the large-scale high sensitivity gas detecting device, used in some local laboratories, is not practically appropriate for the clinical biochemical examination using expiratory air as samples. A practical clinical use of expiratory gas analysis requires an examination device which is small-sized, portable, of high sensitivity, simply operable and superior in safety and rapidity in measurement. Reliability of provided data and economization in use of such examination device are also required. Furthermore, since it is possible that moisture of expiratory air in a container makes dew on a wall of the container to dissolve and adsorb trace amounts of gas components, for such a device it is preferable that expiratory air from a subject (patient) is sucked directly into the device to be subjected to measurement.

SUMMARY OF THE INVENTION

An object of the invention is to provide a bloodless and noninvasive clinical examination device, more particularly, to provide a portable expiratory air examination device which analyzes air samples from a subject, and to determine the concentration of trace amounts of gas components available in the expiratory air samples.

Another object of the invention is to provide an expiratory air examination device which is highly sensitive, readily operable, produces reliable data, and is economical to use.

A further object of the invention is to provide an expiratory air examination device which can be used on infants, aged men and women, and unconscious subjects.

A still further object of the present invention is to provide an expiratory air examination device and an expiratory air examining method which enables rapid measurement in urgent cases, and in any applications where it is necessary to examine several subjects as quickly as possible.

DETAILED DESCRIPTION OF THE PREFERRED EMBODIMENTS

The foregoing circumstances have been zealously studied in order to develop a practical bloodless and noninvasive clinical examination device and method using expiratory air as a sample and to achieve the present invention which will be detailed hereafter.

The expiratory air examination device according to the present invention employs the exhaled air of humans (or animals) as samples, and separates and measures trace amounts of chemical substances in the exhaled air to obtain various clinical biochemical information. The term "bloodless" refers to an examination method which employs specimens other than blood, and the term "noninvasive" means "not breaking", and refers to an examination method wherein samples are collected without hurting the patient or subject.

The expiratory air examination device according to the present invention generally comprises an expiratory air sucking portion, a sample weighing portion, a carrier gas feeding portion, a detecting portion and an arithmetic processing portion. The detecting portion employs a specialized construction, so as to have high sensitivity and to allow it to be small-sized as required for portability.

The analysis of gases generally involves gas chromatography and uses various detectors depending on the gases involved, and the specific purposes of the analysis. The examination device according to the present invention adopts a separator column, particularly a capillary column, for allowing measurement of a plurality of items and a for allowing rapid measurement. The device uses as the detector a PID (Photo Ionization Detector), IMS (Ion Mobility Spectrometer) or ECD (Electron Capture Detector), wherein light or radiation is applied to ionize the gas component of the expiratory air to be detected, so that measurement signals are output corresponding to the amount of ionization of the gas component. Among these detectors, the PID sensor is most preferable, since it does not employ radiation.

This type of detector used in the present invention does not involve the burning of hydrogen gas as in a FID (Flame Ionization Detector) or FPD (Flame Photometric Detector). The absence of such a sensor allows the expiratory air measuring device to be safe and small-sized, and also of high sensitivity and high accuracy in comparison with FID and FPD technologies. There is a further advantage of not employing FID and FPD technologies, in that inexpensive air or nitrogen gas can be used as carrier gas. Also, APIMS (Atmospheric Pressure Ionization Mass Spectrometry) which is highly sensitive and accurate, is nevertheless not applicable to the present invention because of size limitations. Furthermore, detectors having high sensitivity and high accuracy such as a controlled-potential electrolysis gas sensor might be selectively used, i.e., its use might be limited to gases such as carbon monoxide or hydrogen compounds. Hence, such a detector is also not applicable to the present invention.

The expiratory air sucking portion is adapted to feed expiratory air (expiratory gas) to the sample weighing portion. The expiratory air sucking portion comprises an expiratory air collector, such as a mouthpiece or a mask, for collecting expiratory air, and a collecting tube (a sampling probe) mounting the expiratory air collector at one end. The expiratory air sucking portion, particularly, the collecting tube (sampling probe) is preferably heated at its inner surface to human body temperature or higher temperatures, for example, 36° to 100° C., more preferably 40° to 50° C. This prevents moisture from the expiratory air from condensing on and sticking to an inner wall of the collecting tube, where it might dissolve and adsorb an aimed gas component. For heating the collecting tube, a heating element may be disposed circumferentially on or inside the collecting tube. Alternatively, the tube may be made of a material having itself heat build-up and sheathed with insulating material. Also, the collecting tube may include a temperature adjuster mechanism. The expiratory air collector may be disposable, for sanitary purposes.

The apparatus may include a feature in which expiratory air is collected first in a separate expiratory air collecting means such as a large injector or a balloon (but not directly blown into the examination device) and is then fed into the device through the collecting tube. Alternatively, expiratory air collected in a predetermined amount by a syringe may be injected from an expiratory air sample injecting portion formed at the upper stream side of the column. In these cases, the expiratory air collecting means, i.e., the injector, balloon, and syringe must be kept at specific temperatures or heated so that the inside of the expiratory air collecting means can be maintained at temperatures higher than human body temperature.

The sample weighing portion collects and holds as an expiratory air sample a predetermined amount of expiratory air fed from the expiratory air sucking portion. The collection of the predetermined amount of air may be carried out by patient's positive blowing to push the expiratory air into the device, or preferably by use of a sampling pump to take in the expiratory air. Using a sampling pump has several advantages. First, expiratory air can be collected readily from infants or unconscious patients. Second, contamination (carryover) on the inner wall of the collecting tube from a previous subject's expiratory air can be purged and removed, by taking in atmosphere or a subsequent patient's expiratory air.

The sample weighing portion may be constructed so that a carrier gas passage is provided partially with two sets of valves to form therebetween a weighing chamber whose front end connects with an end of the collecting tube through a valve. Also, the sample weighing portion may use a known six-way valve (injection valve) or be so constructed that an end of the collecting tube is connected to a cylinder serving as the weighing chamber to feed into the carrier gas passage an expired air sample collected in the weighing chamber. The predetermined amount of gas in the expiratory air sample depends upon the capacity of the detecting portion and may be about 0.05 to 5.0 ml, more preferably 0.1 to 0.8 ml. The sample weighing portion, particularly the weighing chamber, needs to be kept at a constant temperature, which as previously mentioned is higher than human body temperature (the same temperature as the collecting tube), to prevent moisture from sticking and to keep the mass of the expired air sample constant.

The carrier gas feeding portion feeds a carrier gas, which sends the expired air samples to the separation column. A source of the carrier gas is preferably a small-sized gas cylinder in furtherance of the portability goal of the examination device according to the present invention. When the examination device is installed at a fixed position for use, a larger gas cylinder can be used as the carrier gas source. Also, since the invention does not use hydrogen flame, it can employ relatively inexpensive purified air or nitrogen as the carrier gas. Other gases generally used in the art, such as helium and the like, are also usable.

When air is used as the carrier gas, ambient air, rather than compressed air contained in a cylinder, may be used. The air is conveyed by a compression pump. The air cylinder, and in turn, the vessel itself, is heavy and requires a pressure adjuster, so that the examination device when housed therein the air cylinder is subject to considerable wear and tear, especially when used portably. Since the gas cylinders are small for overall portability of the device, their smaller air content leads to frequent air cylinder replacements. The frequent air cylinder replacements in turn can involve significant labor and expense. In contrast, when freely available ambient air is used for the carrier gas, it eliminates the labor and expense from air cylinders replacement, and enables the examination device to be further downsized. When ambient air is used, an air filter, containing adsorbent material or the like, is provided for purifying the ambient air intake, to eliminate the effects of trace gases present in the ambient air.

In detail, ambient air is purified by the device by passing the air through an absorbing filter. The purified air is pressurized by the compression pump and is used as the carrier gas. The absorbing filter is provided for removing particulates (dust) contained found in ambient air, and contaminant (coexistent) molecules which would hinder the aimed examination. The absorbing filter may comprise an absorbent material, such as activated charcoal or zeolitic products, a filter sheet of fiber products or the like, high voltage absorption, or a decomposition means such as an ultraviolet lamp or the like, or any combination of these elements. Also, the compression pump may be a small-sized electric pump which enables compression of 0.5 to 1.0 Kg/cm. Hence, power consumption by the pump together with the detector is small and a battery suffices for a power source. The carrier gas feeding portion may further incorporate such instruments as: a pressure gauge to monitor the stability of the compression pump, a needle valve and a flow meter to control flow of the carrier gas (purified air) to be fed to the separation column, and a three-way solenoid valve to releases the carrier gas into the atmosphere when it is not flowing into the column. Also, a compressed air reservoir may be provided at the lower stream side of the compression pump.

The PID, IMS or ECD detector ionizes oxygen gas to form ozone gas. The ozone gas itself is not detected by the detector, and does not affect the measured values. Although concentration of the ozone gas is about 10 to 50 ppm, the byproduct of ozone is undesirable since the expiratory air examination is usually carried out in hospitals where the presence of ozone is unwelcome. Thus, it is preferable to additionally provide an ozone treatment tank at the lower stream side of the detector to absorb the ozone gas or reduce the ozone gas to diatomic oxygen gas by using ultraviolet light. Alternatively, a portion or all of the waste carrier gas may be mixed, in a mixing tank, with a first purified air (which passed through a first absorbing filter) and then passed through a second absorbing filter to be a second purified air which is then given pressure by a compression pump and is used as a carrier gas. In the mixing tank, ozone gas contained in the waste carrier gas oxidizes a sensible content which remains in the first purified air and causes noises that are sensed by the detector. The first purified air is thereafter passed through the second absorbing filter made of activated charcoal or zeolitic products, thereby providing highly purified air. Since moisture in the air does not have an effect on the measurement, dehumidification is not so important. A dehumidifying agent may be included partially in the absorbing filter when required.

Furthermore, the detecting portion comprises a column for separating an aimed gas component contained in an expiratory air sample, and a detector. The column employs a capillary column but may alternatively use a packed column depending on the sort of gases to be detected. Fillers for the packed column and liquid layers of the capillary column are selected, corresponding to specific gases to be detected. The fillers are selected from various kinds of fillers and liquid layers hitherto known in consideration of such conditions required for the examination as measurement accuracy, reproducibility and rapidity. In this case, when only one kind of gas is detected, a corresponding filler most suitable for determining the gas may be selected. However, certain items (diseases) subject to examination may require measurement of a plurality of gases to be detected, and a plurality of gases may be measured for examining a plurality of items at a time for labor-saving purposes. In such cases, when no ideal or suitable filler is found, a plurality of columns are used in parallel or a plurality of detectors are employed. Also, the separation column is required to be kept at a constant temperature for providing reproducibility. It is preferable to keep the column at a temperature as low as possible, for example, room temperature (20° C.) to 50° C. to prevent decomposition or deterioration of gases to be detected.

The photo ionization detector (PID) is most suitable for the detector employed in the present invention. The PID utilizes the phenomenon that when light (ultraviolet) is applied to an aimed gas component having higher energy than the ionization potential of the gas, ionization results. The amount of ionization of the gas is converted to an ionizing current for producing an output with electrodes, so that concentration of detected gas components is determined from magnitude of ionizing current. An IMS (Ion mobility spectrometer) is also suitable for the invention. The IMS is constructed so that the gas component subjected to detection is ionized by β rays and cyclically shut and released by a shutter to be fed into a moving layer under atmospheric pressure in which layer ions are fractionated depending on their ionic properties (size, mass and shape). The ions have specific drift times, whereby mobility of the ions are compared with a pattern data (algorithm) of standard contents memorized previously in a microprocessor to make identification of an aimed gas component. Also, an ECD (Electron Capture Detector) employs B rays as an ionizing source, and ionizes an aimed gas component to detect the gas component with high sensitivity, for making identification. Any ion analysis techniques which will be developed separately from the above techniques in the future and be safe and small-sized with high sensitivity and high accuracy in use may be also applicable to the present invention.

A principal portion of the arithmetic processing portion is a microcomputer, which contains an operating program for controlling the expiratory air examination device. The microcomputer receives the measurement signals output from the detector and processes these signals. The microcomputer calculates the concentration of an aimed gas component by use of a previously memorized working curve, and stores the computed concentration as clinical examination data or outputs the data on an indicating device (display) or a recording device (printer). The microcomputer may also receive input signals from a keyboard.

The examination device constructed as above according to the present invention may be used as follows.

(1) The sample collector is first put to or on patient's mouth or face. The measurement start button on the keyboard is depressed and simultaneously the patient exhales for a few seconds. When the subject (patient) has held their breath for about 10 to 20 sec before blowing breath through the collector and a very small amount of expired air just blown is discarded, the remainder can be regarded as alveolar air component equilibrating with mixed venous blood gas partial pressure, thereby enabling a measurement with excellent reproducibility.

(2) The expiratory air is sucked through the collecting tube, and a part of the air is collected in the weighing chamber and fed into the separation column by the carrier gas.

(3) Trace amounts of an aimed gas component of the expiratory air separated in the column is ionized in the detector and the amount of ionization of the gas is detected with high sensitivity.

(4) The output from the detector is arithmetically processed and the concentration of the aimed gas component is computed on the basis of a previously memorized working curve. The results are stored as clinical examination data or output on an output device. Each measurement requires from a few seconds to several minutes, depending upon the kinds of gases to be detected, so that the concentration of a single or a plurality of specific gas components contained in the expiratory air can be measured rapidly and accurately.

Next, an examination of expiratory air using the expiratory air examination device according to the present invention will be detailed. Exemplified are examinations for diabetes and hyperammonemia in comparison with the conventional analysis employing blood and urine sampling techniques.

Diabetes can be examined by screening urine (examining urine sugar values), precision examinations with blood (examining blood sugar, glucose tolerance test, HbAlc, Saccharified Hb test, etc) and measurement of ketone body in the patient's blood (ketone body is a generic name of the three components, acetone, acetoacetic acid and 3-hydroxybutyric acid). Diabetics are heard to have an increase of ketone body in their blood, particularly, 3-hydroxybutyric acid (3-OHBA). Ketone body in blood or urine (screening) is recently measured by nitroprusside test: a test which in fact cannot accurately measure 3-hydroxybutyric acid. A commercially available product (KETOLEX made by Sanwa Chemical Co.,Ltd.) employs colorimetry using 3-hydroxybutyrate dehydrogenase to enable measurement of 3-hydroxybutyric acid, but it is costly and the reagent cannot be preserved for a long term. Also, concentration in urine does not correlate well with that in blood, and the screening has additional problems, so that only the blood analysis is relied on.

The ketone body has an in-vivo (in blood) relationship of equilibrium and decomposition with respect to acetoacetic acid (AcAc), as represented in the following formula.

Ac←AcAc⇌3-OHBA

The ketone body appears or is discharged, mainly in the form of acetone (Ac). In the expiratory air found in air vessels, Ac, AcAc, and 3-OHBA are measured in amounts correlating with their concentration in the patient's blood. By use of the examination device according to the present invention, ketone body (particularly, acetone, which readily appears in expiratory air) can be measured in a relatively short time without causing the subjects any pain. Additionally, the examination device can be similarly applied to screening of diabetes, fasting, or malnutrition and also to precision examination and monitoring.

In case of liver dysfunction, particularly, in newborn infants and uremia, ammonia shows high toxicity. Quantities of 2 mg/dl or more of ammonia can cause the patients to have intoxication, leading to coma. Patients with serious liver disorders may experience alienation or a clouding of their consciousness. The presence of ammonia in the blood has been previously measured by colorimetric analysis with ammonia separated through various techniques, or applied with enzymes. But, the methods have problems, in that they require special instruments for analysis and advanced techniques for cooling the blood sample after collection or deproteinization. They also require considerable labor, and the tests are hindered by inhibitor substances. Furthermore, ammonia in the blood is generally present in trace amounts and increases after the blood is collected and left to stand. Hence, ammonia in the blood is to be measured as rapidly as possible by use of a measuring method of high sensitivity. The conventional methods do not meet their purpose, and have problems in measurement accuracy.

In contrast, the examination device according to the present invention can rapidly measure the concentration of ammonia correlating with the ammonia levels in the blood by merely fractionally measuring the amount of ammonia in the patient's expiratory air. However, this measurement causes the patient no pain.

The expiratory air examination device according to the invention can make several additional analytical measurements of most of the gas components contained in the blood, in addition to the foregoing measurement of ketone body and ammonia. In detail, the examination device can carry out rapid measurement of plural components of lower fatty acid serving as an index of liver function test (hepatic insufficiency), simultaneous rapid measurement of ammonia and amine serving as an index of hyperammonemia test, simultaneous rapid measurement of hydrogen sulfide and mercaptan caused from liver diseases (hepatic insufficiency) or oral surgery disorder (ozostomia), simultaneous rapid measurement of lower saturated hydrocarbon (ethane, propane, butane, pentane, etc) serving as an index of existence or non-existence of formation of lipoperoxide (index factor of carcinogenesis), and rapid measurement for monitoring states of intoxation due to chemical substances (intoxation from CO, alcohol or other volatile toxic chemical substances) and grasping pretreatment conditions.

The examination device enables measurement of phenylacetic acid caused from phenylketonuria, the measurement of which is usually carried out by urine analysis. Methane and hydrogen (caused from alimentary canal passing-disturbance or intestinal abnormal fermentation) are not measurable with blood and urine samples, but may be analyzed with the present device. The device can also detect the presence of a lower hydrocarbon, such as ethane and pentane (caused from exposure of organic solvents, lipoperoxide). Sulfuric malodorous components such as hydrogen sulfide and mercaptan sometimes cannot be judged from which they are caused visceral affection or oral surgical diseases. In this case, since mouthwashing with clean water or an aqueous solution of hydrogen peroxide or removal of coating of tongue can eliminate influence from ozostomia, expiratory air may be measured before and after mouthwashing or the like to detect specific gases from the causes.

Furthermore, in case of visceral disorders, specific gas components do not necessarily directly correspond to respective disorders, similarly to the examinations with blood and urine. For the screening, a certain kind of gas may be measured as in the above example, to infer the degree of a corresponding disease. Also, liquid layers of the column and measurement programs may be set to enable detection of a plurality of gas components so as to carry out measurements for a plurality of disease items or measurement of a single disease item with high accuracy. Hereunder exemplified are groups of aimed gases in measurement of a plurality of disease items.

(a) Diseases of adult people: screening
acetone diabetes
ammonia liver, kidney
methyl mercaptan liver, kidney
acetaldehyde liver, kidney
pentane formation of lipoperoxide
(b) Newborn infants, infants
ammonia hyperammonemia (inborn error of metabolism)
phenylacetic acid phenylketonuria (inborn error of metabolism)
isovaleric acid isovalericacidemia (inborn error of metabolism)
methyl mercaptan liver, kidney The examination device of the invention, particularly in those embodiments provided with a sampling pump, is adapted to automatically commence operation when the patient merely exhales into the device. Hence, the examination can be readily carried out, irrespective of ages, sex, states of disease of the patient, for any subjects, including: aged men and women, newborn infants, infants, unconscious patients or serious marasmic patients. Furthermore, since the examination device is small-sized and readily operable, it is broadly applicable to be used for screening and diagnosis of metabolic or toxic diseases, tolerance tests, monitoring of the course of diseases, and as a testing instrument for pre-hospital treatment as in an ambulance.

EMBODIMENTS

Figure 1:
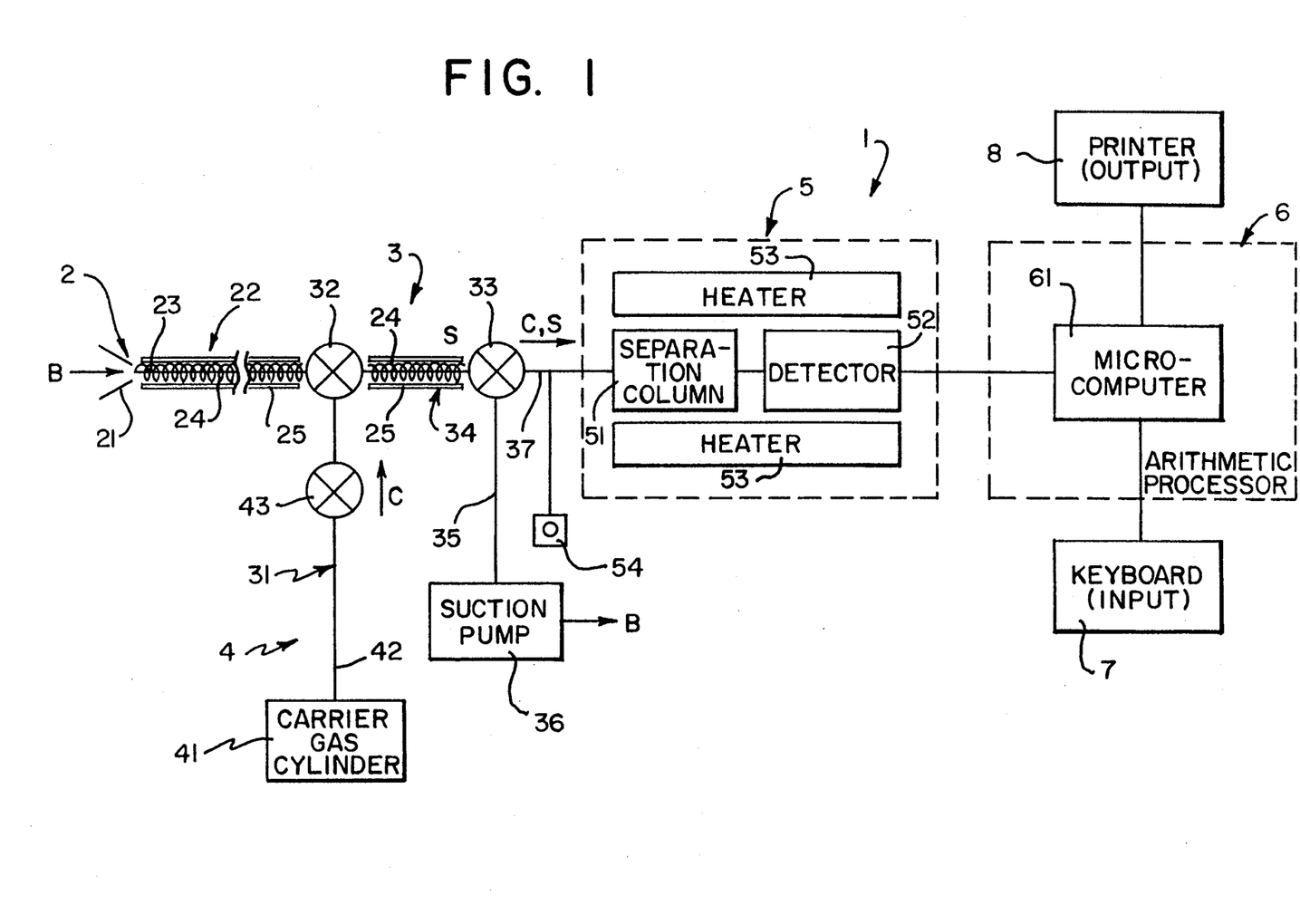
FIG. 1 is a block diagram showing an expiratory air examination device, according to the present invention.

Next, the invention will be detailed with referring to the examples shown in the attached drawings. It is important to note that the present invention should not at all be limited to the features shown in the drawings. The drawings are illustrative only. FIG. 1 is a block diagram showing an expiratory air examination device i according to the present invention. The examination device i comprises an expiratory air sucking portion 2, a sample weighing portion 3, a carrier gas feeding portion 4, a detecting portion 5, an arithmetic processing portion 6, a keyboard 7 serving as an input device and a printer 8 serving as an output device.

The expiratory air sucking portion 2 comprises an expiratory air collecting mask 21 serving as an expiratory air collector and a collecting tube 22 mounting the mask 21 at the utmost end. The collecting tube 22 comprises a Teflon pipe 23 (1–5 mm in inner diameter and about 1 m in length) mounting thereon a heater 24, sheathed with a heat insulating material 25, so that the pipe 23 is heated on the inside to prevent the moisture in expiratory air from sticking to the inner surface of the pipe 23. The heating is carried out at a temperature of 36° to 100° C., for example, 40° C. adjusted by a controller. A mouthpiece may be usable instead of the expiratory air collecting mask 21.

The sample weighing portion 3 has a carrier gas passage 31 provided partially with two sets of three-way solenoid valves 32 and 33, forming therebetween a weighing chamber 34 to the front end of which, an end of the collecting tube 22 is connected through the solenoid valve 32. The weighing chamber 34 is constructed similarly with the collecting tube 22 by use of the same materials, so that the weighing chamber 34 is similarly heated at about 40° C. The capacity of the weighing chamber 34 is about 0.5 ml. A suction pump 36 is connected to the rear solenoid valve 33 through an exhaust tube 35. Also, a sample injection tube 37 connects the solenoid valve 33 with a column 51, so that the carrier gas passage 31 comprises a carrier gas feeding pipe 42, the weighing chamber and the sample injection tube 37. If the suction pump 36 is omitted, a patient (subject) may blow through the collecting tube to force his or her expiratory air.

If a predetermined amount of expiratory air is collected in a syringes instead of having the subjects directly blow into the collecting tube (including situations where a balloon or large-sized injector is used), the apparatus may be modified so that instead of the expiratory air sucking portion 2, an expiratory air sample injecting portion (inlet) 54 is formed at the upper stream side of the column as shown in FIG. 1, through which portion 54 a weighed expiratory air sample is fed into the column.

Figure 2:
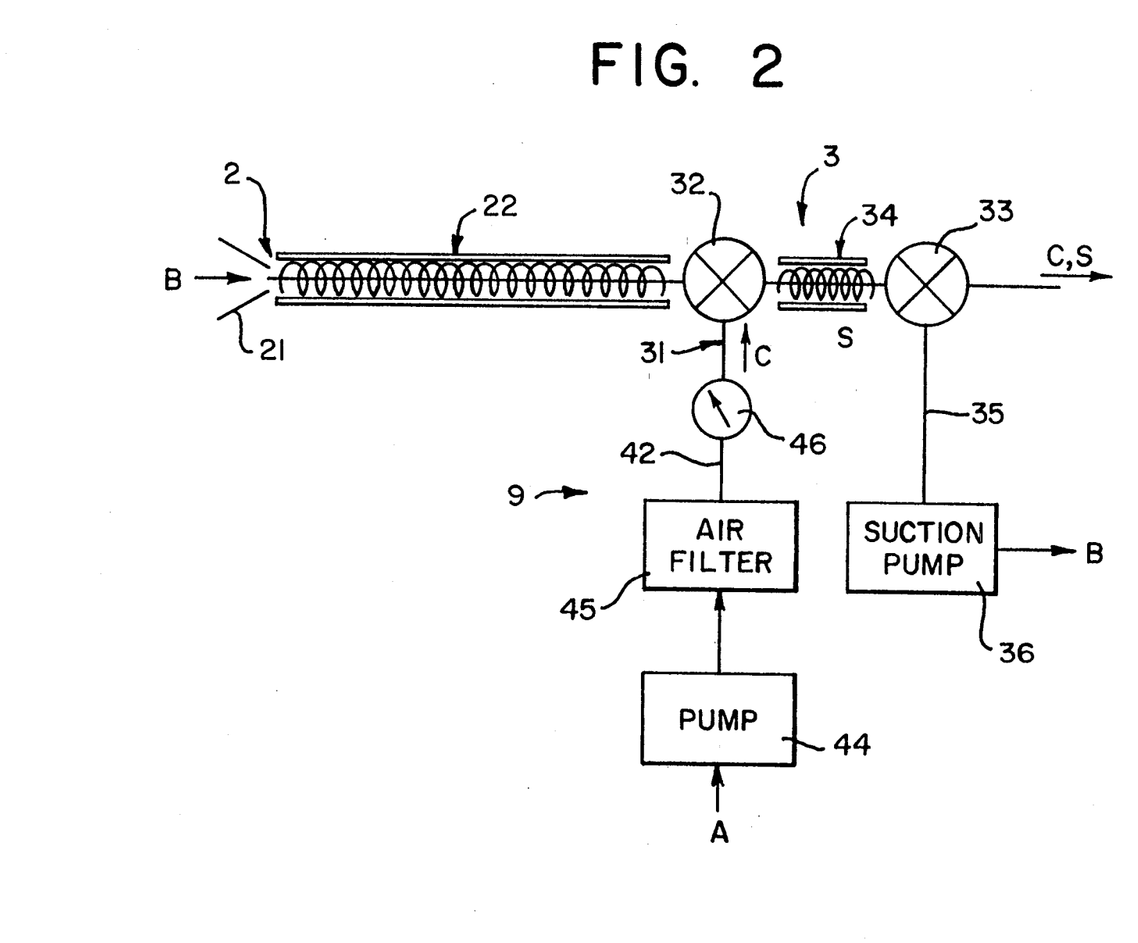
FIGS. 2, 3 and 4 are block diagrams showing modified examples of the carrier gas feeding portion.

The carrier gas feeding portion 4 comprises a small-sized air cylinder 41 containing purified air and the carrier gas feeding pipe 42 connected to the solenoid valve 32. Reference numeral 43 designates a three-way solenoid valve. A carrier gas feeding portion 9 shown in FIG. 2 is a modified example wherein without use of the air cylinder 41, ambient air surrounding the device is given pressure by a compression pump so it may be used as a carrier gas. When ambient air is used, to eliminate influences of trace amounts of gas component in the taken ambient air, an air filter 45 having an absorbent layer is required. Reference numeral 46 designates a flow meter.

Figure 3:
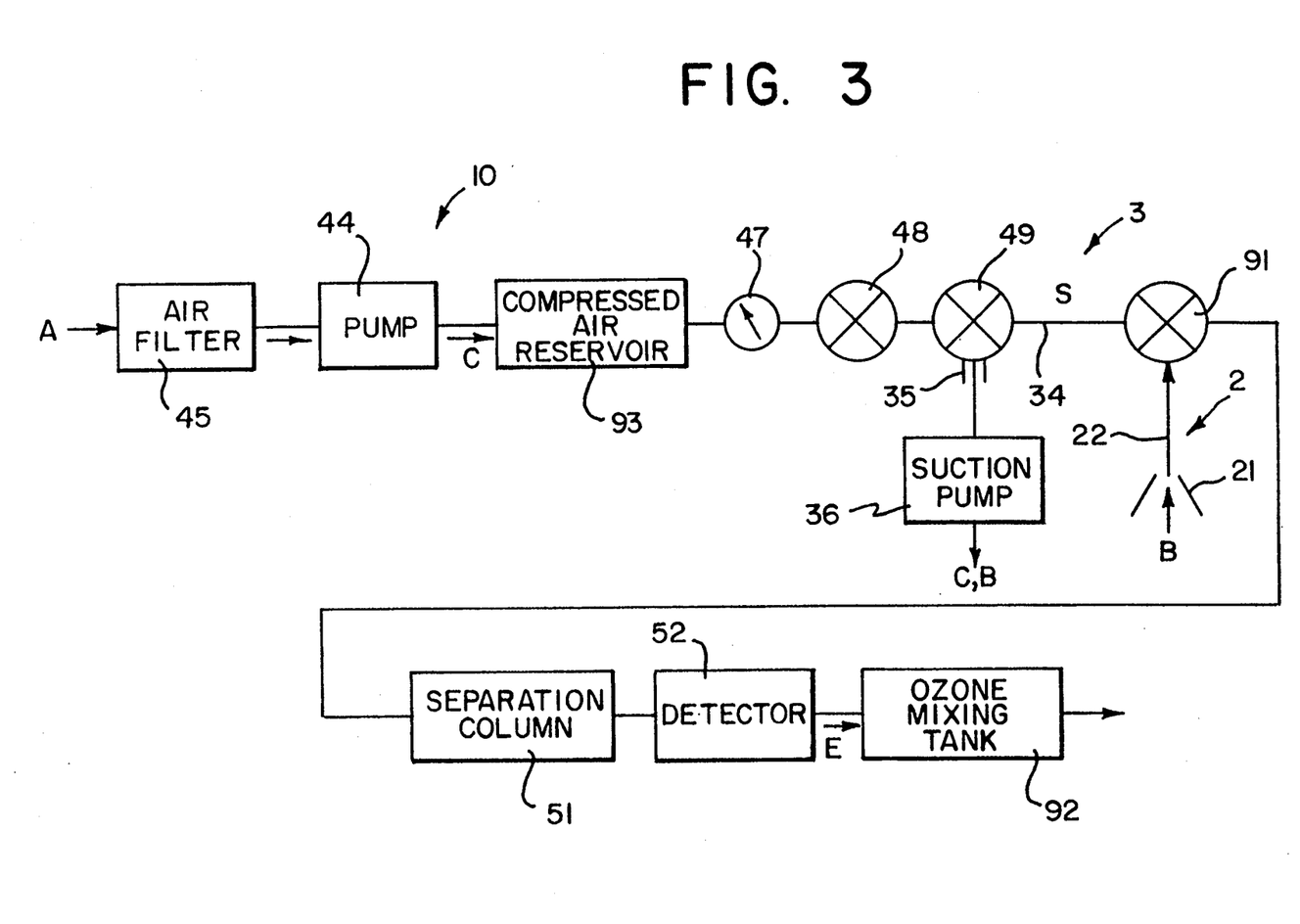
Figure 4:
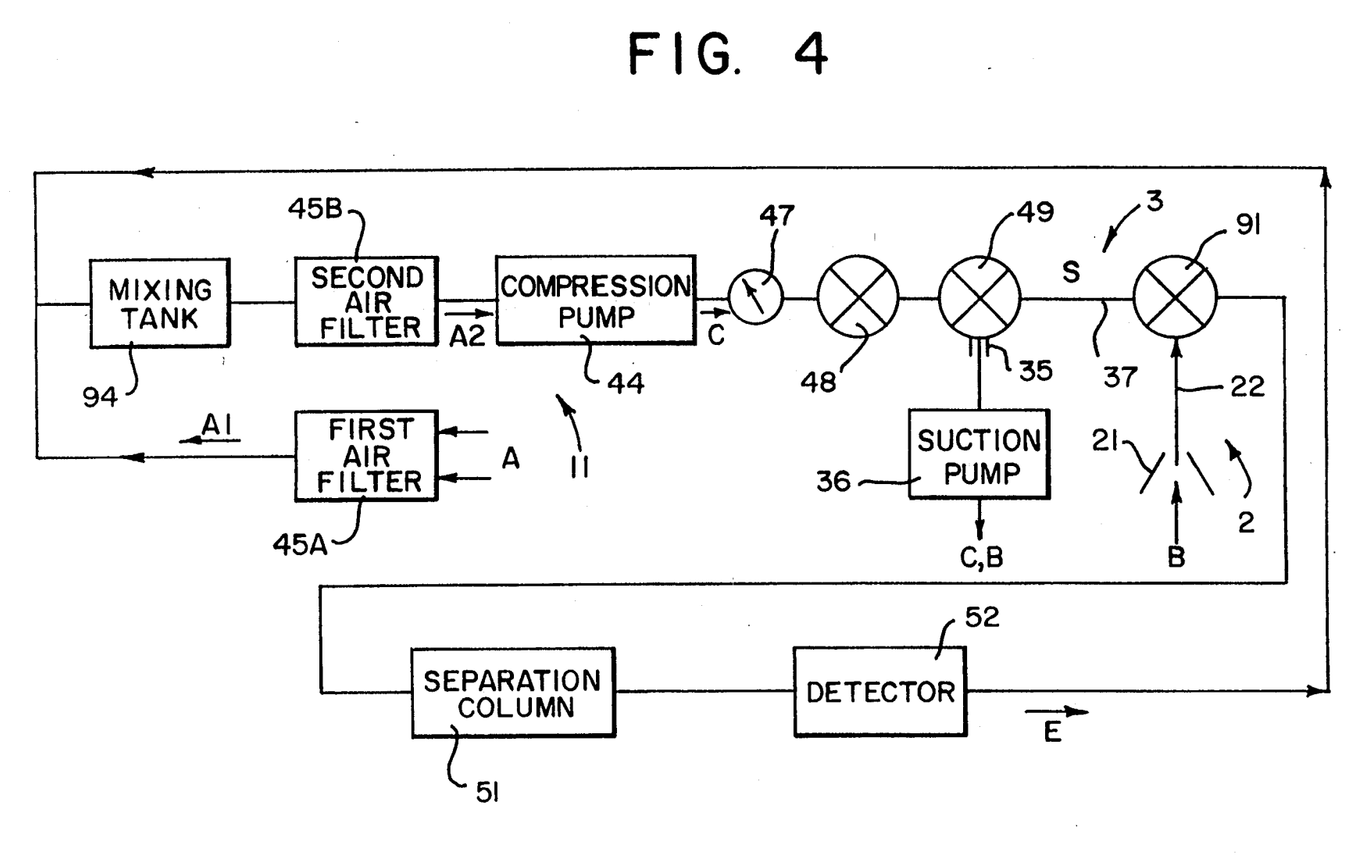

FIGS. 3 and 4 are block diagrams showing further modified examples of the carrier gas feeding portion using the compression pump. In a carrier gas feeding portion 10 shown in FIG. 3, air A taken from the atmosphere or ambient air is passed through the air filter 45 to remove particulates (dust) or contaminant coexisting molecules, and is then pressurized by the compression pump 44 to become a carrier gas C. The carrier gas goes through a flow adjuster means such as a pressure gauge 47 and a needle valve 48, to a three-way solenoid valve 49. The carrier gas C, when fed into a column 51 through the three-way solenoid valve 49, carries an expiratory air sample S stored in the weighing chamber 34 into the column. Aimed gas components contained in the sample are separated orderly in the column and moved into a detector 52, so that the detector 52 outputs measurement signals to the arithmetic processing portion (not shown in FIG. 3). The carrier gas C, when not fed into the column, may be partially leaked through the exhaust tube 35, connected to the solenoid valve 49. 91 is a three-way solenoid valve or an injection valve in FIG. 3. Furthermore, an ozone mixing tank 92 may be provided at the lower stream side of the detector 52 for removing ozone gas contained in the waste carrier gas. A compressed air reservoir 93 can be employed to enable the working intervals of the compression pump 44 extended.

In a carrier gas feeding portion 11 shown in FIG. 4, air A taken from atmosphere or ambient air is passed through a first air filter 45A, to be removed of particulates (dust) or contaminant coexisting molecules, and becomes a first purified air A1, which is moved into a mixing tank 94. In the mixing tank 94, impurities remaining in the purified air A1 is subjected to oxidation by ozone gas contained in the waste carrier gas E (described later) and further removed at a second air filter 45B to cause the first air A1 to become a second purified air A2 which is then pressurized by the compression pump 44 to become a carrier gas C. Other features in this case are the same as that shown in FIG. 3.

Figure 5:
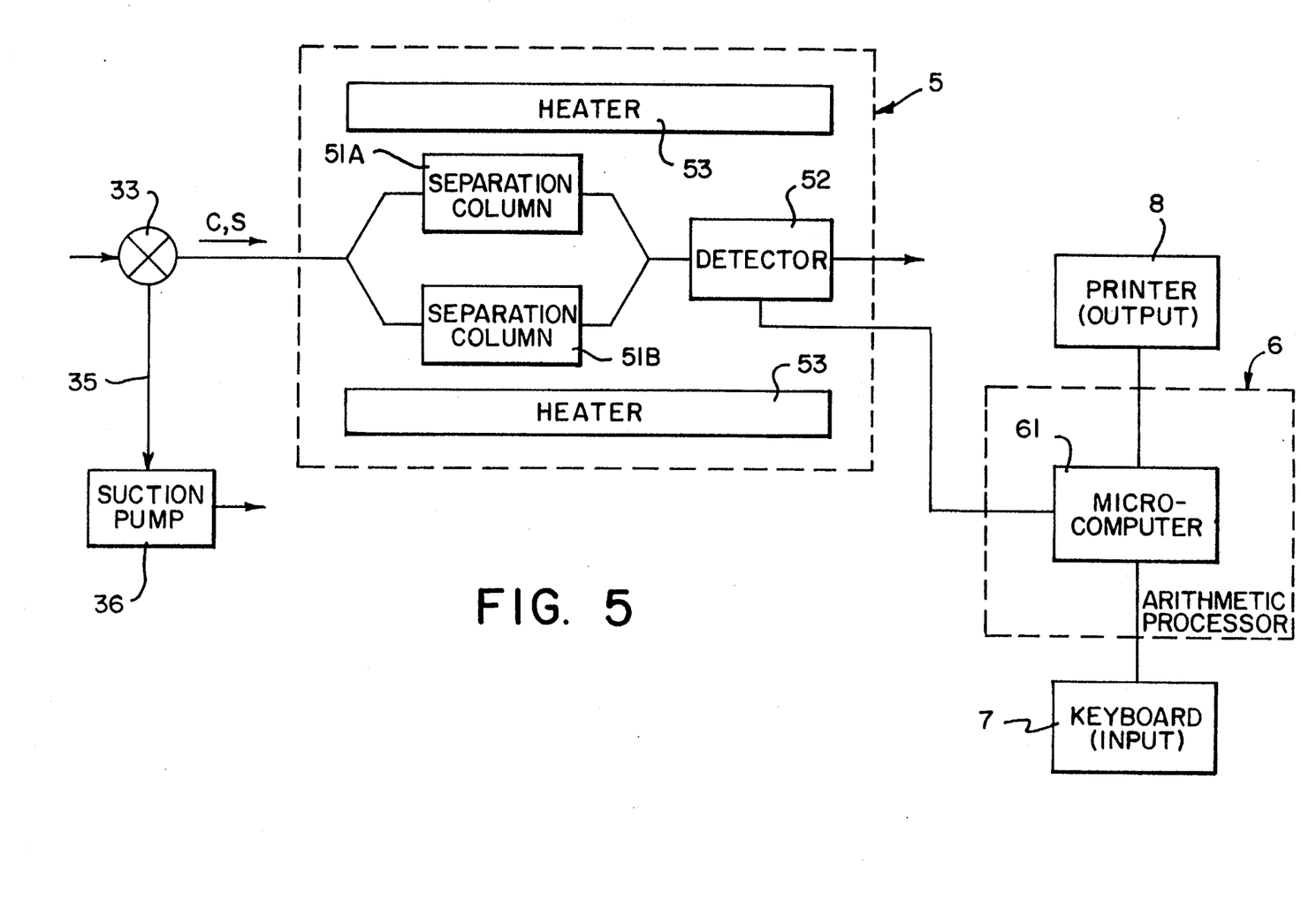
FIG. 5 is a partial block diagram showing a modified example of the detecting portion.

The detector 5 comprises a column 51 for separating aimed gas components contained in the expiratory air, and a detector 52. The column 51 employs a capillary column and the detector 52 employs a photo ionization detector (PID). The PID applies ultraviolet radiation to the aimed gas components, having energy larger than ionization potential of the aimed gases, to ionize the gases. An amount of ionization of the gases is converted to an ionizing current by use of electrodes and is output. The detector is quite small-sized but has high accuracy and high sensitivity. The column 51 and detector 52 are kept at a constant temperature of about 40° C. by a heater 53. A liquid layer in the column is selected from known liquid layers to allow specific components of aimed gas, for example, ketone body to have retention times of several dozen seconds to several minutes. Measurement of a plurality of gases may be required, depending upon specific disease items to be examined. A plurality of gases may be measured to examine a plurality of disease items at a time for labor-saving purposes. In such case, when no ideal filler or liquid layer is found, a plurality of columns 51 may be used in parallel as shown in FIG. 5 to improve separation accuracy. A plurality of columns 51 and a plurality of detectors 52 may be included in the device.

A principal portion of the arithmetic processing portion 6 is a microcomputer 61 which contains an operating program for controlling the whole expiratory air examination device as it receives measurement signals that are output from the detector 52 to process the signals, computes concentration of an aimed gas component by use of a previously memorized working curve, outputs the computed concentration as a clinical examination data on a printer, or receives input signals from a keyboard to output operation commands for specific parts.

To use the examination device, a main switch on the keyboard 7 is first turned on to attain constant temperature at the specific parts where the temperature is critical. The expiratory air collecting mask 21 is fit on the patient's face, and the measurement start button on the keyboard 7 is depressed. Expiratory air B is exhausted outside by the suction pump 36 while a part of the air B fills the weighing chamber 34, to collect a sample of a predetermined amount of expiratory air S, by closing the solenoid valves 32 and 33. The subject blows expiratory air into the device for about 5 sec. The expiratory air sample S is fed into the column 51 by the carrier gas C, sent from the air cylinder 41 or the like, and is separated and fractionated depending on specific retention time of the aimed gases. It is ionized orderly in the detector 52, so that the amounts of ionization of the gases are converted to electric signals to be output. The electric signals are processed by the arithmetic processing portion 6 so that the concentration of aimed gas components contained in the expiratory air (for example, ketone body) are determined by use of the previously memorized working curve.

Measurement ends about 2.5 min after the expiratory air of the subject is sucked into the device.

Figure 6:
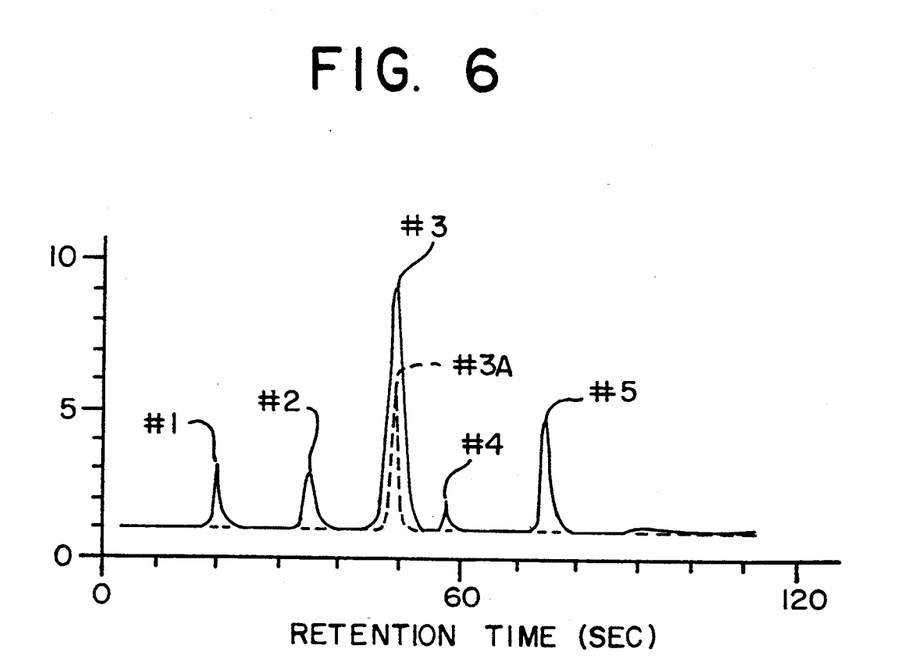
FIG. 6 is a gas chromatogram of ketone body (acetone) measured by the device according to the present invention, wherein the broken line shows the measurement using a standard substance as a sample and the solid line indicates an expiratory air sample taken from a diabetic.

FIG. 6 is a gas chromatogram measurement of acetone representing ketone body and serving as an examination index of diabetes, malnutrition and fasting. Measurement was carried out with a 45 degree celsius column temperature and a carrier gas (purified air) flow 7.0 ml/min. The broken line in FIG. 6 shows the results from a measurement of a standard gas containing acetone 5 ppm (nitrogen balance). Acetone was detected with a retention time of 50.5 sec (peak #3A). The solid line shows a result of a measurement of expiratory air of a visitor patient with diabetes (not treated for insulin) and an acute peak (peak #3) was recorded at a position corresponding to a retention time 50.3 sec. It is determined from this that the expiratory air of the patient in this instance contains about 8 ppm of acetone. The other peaks show specific components contained in the expiratory air, peak #2 being identified as acetaldehyde and peak #5, ethanol. Peaks 1 and 4 were unidentified. As seen from the above, ketone body (acetone) serving as an index component can be measured in a short time without having being hindered by other components contained in the expiratory air.

EFFECTS OF TEE INVENTION

As clearly seen from the above, the present invention relates to an expiratory air examination device and method for clinical use, which analyzes an expiratory air sample of a subject, to measure aimed trace amounts of gases contained in the expiratory air sample. An expiratory air sample fed from the expiratory air sucking portion is sent through a column to a detector which ionizes trace amounts of aimed gas components contained in the expiratory air by applying ultraviolet light or radiation to the aimed gas components so as to detect such gas components, thereby measuring the concentration of the gas components. Hence, the invention has the following characteristics.

(1) The invention uses as a sample the expiratory air which is bloodless and noninvasive and does not cause a patient a pain, a feeling of fear or pressure. Hence, the burden imposed on the patient in relation to repeated measurement of tolerance tests and continuous observation can be completely eliminated.

(2) Operation of the device consists of merely having the subjects exhale into the expiratory air collector. Hence, an operator does not need to have special training to use the device. Also, when the device is provided with a sampling pump, it can readily collect an expiratory air sample from infants or patients with a serious illness or in a state of unconsciousness.

(3) Since the expiratory air collecting tube (sampling probe) is heated at its inside wall, there is no loss of trace amounts of aimed components contained in the expiratory air, and measured values can be obtained with accuracy and reproducibility.

(4) Since a detector is employed which requires no burning of hydrogen and enables measurement with high sensitivity in a short time, the examination device can be made small-sized, readily operable and enable rapidity of measurement with a low cost for each examination.

(5) Since the device can be small-sized, it can be used as a bedside instrument or mounted on an ambulance without much limitation as to where it may be used.

Also, measurement results can be obtained and recorded quickly (in 2–3 min), so that it provides a wide range of clinical application. For example, the measurement results can be instantly used as clinical data.

(6) The device can use air or nitrogen as a carrier gas, allowing it to be operated at low cost. Also, the device adapted to use ambient air as a carrier gas, by purifying the ambient air in the machine, can be further downsized and made light-weight and reduces the operating cost.

(7) The waste carrier gas is passed through the ozone treatment tank and mixed with ambient air taken in to the device to thereby treat ozone gas, preventing contamination to the environment.

(8) Adoption of a plurality of columns enables measurement of a plurality of aimed gases (each having a different retention time) in a short time to improve the rapidity of the examination.

(9) The examination device does not at all cause subjects pain and provides examination results instantly, so that diseases can be located at an early stage.

(10) The invention can provide measurement results more readily and rapidly in comparison with examinations involving blood. The invention can also can provide considerable information in comparison with examinations involving urine or other bloodless and noninvasive clinical examination methods, so that the invention can rapidly increase the number of obtainable clinical reports. As a result, such reports of measurement of a specific gas which hitherto are unknown, may lead to large contributions to medical science, such as the diagnosis of a new disease or identification thereof and interpretation of unidentified phenomena which is presently unpredictable.

What is claimed is:

1. An expiratory air examination device comprising:
   an expiratory air sucking portion for receiving expiratory air;
   a sample weighing portion connected to the air sucking portion holding as an expiratory air sample a predetermined amount of a portion of the expiratory air fed from the expiratory air sucking portion;
   a separation column connected to the sample weighing portion for separating a desired gas component in the expiratory air;
   a carrier gas feeding portion connected to the sample weighing portion sending a carrier gas which feeds the expiratory air sample into the separation column;
   a detecting portion connected to the separation column, including detector means for ionizing the expiratory air sample by application of ultraviolet radiation, for detecting trace amounts of the desired gas component contained in the expiratory air sample, and for outputting measurement signals corresponding to an amount of ionization of the desired gas component; and
   an arithmetic processing portion connected to said detecting portion for processing the measurement signals and for computing concentration of the desired gas component based on a previously memorized working curve.

2. A device as in claim 1, wherein the expiratory air sucking portion comprises an expiratory air collector and a tube mounting the expiratory air collector at an utmost end, the tube having any one of a heating element and heat generating material, the tube being sheathed on an outer periphery with a heat insulating material.

3. A device as in claim 2, wherein the air collector has a form selected from a group consisting of a mouth piece and an air collecting mask.

4. A device as in claim 2, wherein said heating element is provided circumferentially about the tube.

5. A device as in claim 2, wherein said heating element is provided inside of the tube.

6. The device of claim 2, wherein the tube is a collecting tube.

7. The device of claim 2, wherein the tube is a sampling tube.

8. A device as claim 1, wherein the carrier gas feeding portion comprises means for feeding a purified air serving as a carrier, including an adsorbing filter, and a compression pump for giving pressure to air passing the adsorbing filter and a flow adjuster.

9. A device as in claim 1, wherein the arithmetic processing portion includes means for storing the computed concentration of the desired gas component as indicative of clinical examination data.

10. A device as in claim 1, wherein the arithmetic processing portion includes means for outputting the computed concentration of the desired gas component on any one of an indicating device and a recording device.

11. A device as in claim 1, wherein the carrier gas feeding portion comprises a first adsorbing filter connected to a mixing tank for mixing air passed through the first adsorbing filter with a waste carrier gas from the detector portion, a second adsorbing filter connected to the mixing tank which treats the air from the mixing tank, a compression pump connected to the second adsorbing filter and a flow adjuster connected to the compression pump.

* * * * *